US012318409B2

United States Patent
Lee et al.

(10) Patent No.: US 12,318,409 B2
(45) Date of Patent: Jun. 3, 2025

(54) PHARMACEUTICAL COMPOSITION FOR PROMOTING OSTEOGENESIS, COMPRISING OSTEOBLAST-DERIVED MITOCHONDRIA

(71) Applicant: Seoul National University R&DB Foundation, Seoul (KR)

(72) Inventors: Yun-Sil Lee, Seoul (KR); Na-Kyung Kim, Seoul (KR); Joonho Suh, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 710 days.

(21) Appl. No.: 17/614,635

(22) PCT Filed: May 29, 2020

(86) PCT No.: PCT/KR2020/007015
§ 371 (c)(1),
(2) Date: Nov. 29, 2021

(87) PCT Pub. No.: WO2020/242250
PCT Pub. Date: Dec. 3, 2020

(65) Prior Publication Data
US 2022/0226387 A1 Jul. 21, 2022

(30) Foreign Application Priority Data
May 30, 2019 (KR) .................. 10-2019-0063976

(51) Int. Cl.
*A61K 35/32* (2015.01)
*A61P 19/08* (2006.01)
*C12N 5/077* (2010.01)

(52) U.S. Cl.
CPC .............. *A61K 35/32* (2013.01); *A61P 19/08* (2018.01); *C12N 5/0654* (2013.01)

(58) Field of Classification Search
CPC ....... A61K 35/32; A61P 19/08; C12N 5/0654; C12N 2510/00; C12N 2509/10; A01K 67/027; A01K 67/0275; A01K 2217/206
See application file for complete search history.

(56) References Cited

U.S. PATENT DOCUMENTS

2020/0009198 A1* 1/2020 Choi .................. A61K 9/00

FOREIGN PATENT DOCUMENTS

| KR | 10-2013-0128302 | 11/2013 |
|----|----|----|
| KR | 10-1480982 | 2/2015 |
| KR | 20150093640 | 8/2015 |
| KR | 20180054522 | 5/2018 |
| KR | 20180071030 | 6/2018 |
| WO | 2008137035 | 11/2008 |

OTHER PUBLICATIONS

Pickles et al. (Endo-MitoEGFP Mice: A Novel Transgenic Mouse with Fluorescently Marked Mitochondria in Microvascular Endothelial cells, PLOS ONE, 2013 (Year: 2013).*
Zheng et al. (Mitochondrial Regulation of Stem Cells in Bone Homeostasis, Trends in Molecular Medicine (Year: 2019).*
KIPO, PCT Search Report & Written Opinion of PCT/KR2020/007015 dated Sep. 1, 2020.
Anuradha Kalani et al., "Mitochondrial epigenetics in bone remodeling during hyperhomocysteinemia", Mol Cell Biochem (2014) 395:89-98, Jun. 18, 2014, DOI 10.1007/s11010-014-2114-3.
Kazuhide Hayakawa et al., "Transfer of mitochondria from astrocytes to neurons after stroke", Nature. Jul. 28, 2016;535 (7613):551-5 vesicle-based interorgan transport of mitochondria from energetically stressed 1853-1868, Sep. 7, 2021.
Clair Crewe et al., "Extracellular vesicle-based interorgan transport of mitochondria from energetically stressed adipocytes", Cell Metabolism 33, 1853-1868, Sep. 7, 2021.
Chen-Xi Zheng et al., "Mitochondrial Regulation of Stem Cells in Bone Homeostasis", Trends in Molecular Medicine, vol. 26, No. 1, pp. 89-104, May 21, 2019.

* cited by examiner

*Primary Examiner* — Robert A Wax
*Assistant Examiner* — John Seungjai Kwon
(74) *Attorney, Agent, or Firm* — LEX IP MEISTER, PLLC

(57) ABSTRACT

The present invention relates to a pharmaceutical composition for promoting osteogenesis and a pharmaceutical composition for treating bone diseases, the compositions comprising osteoblast-derived mitochondria as an active ingredient.

14 Claims, 13 Drawing Sheets

FIG. 2
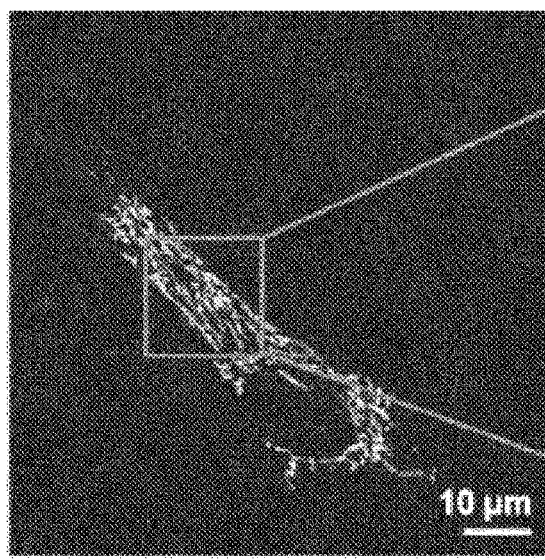
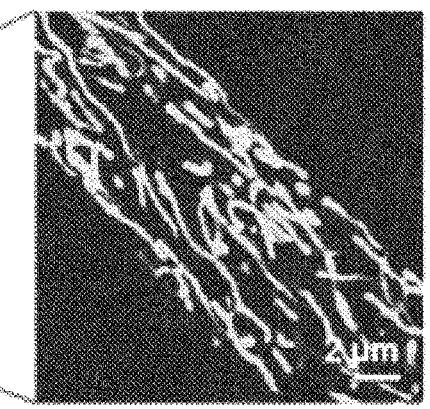
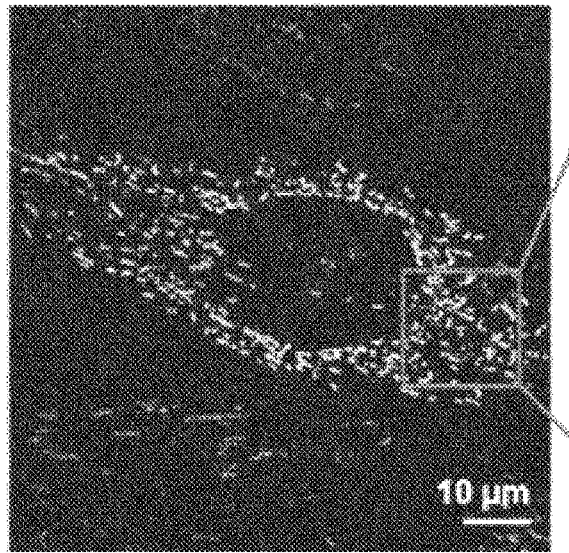
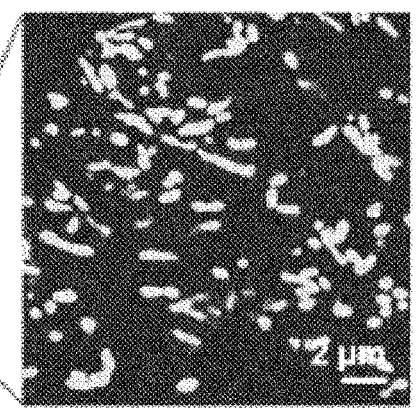

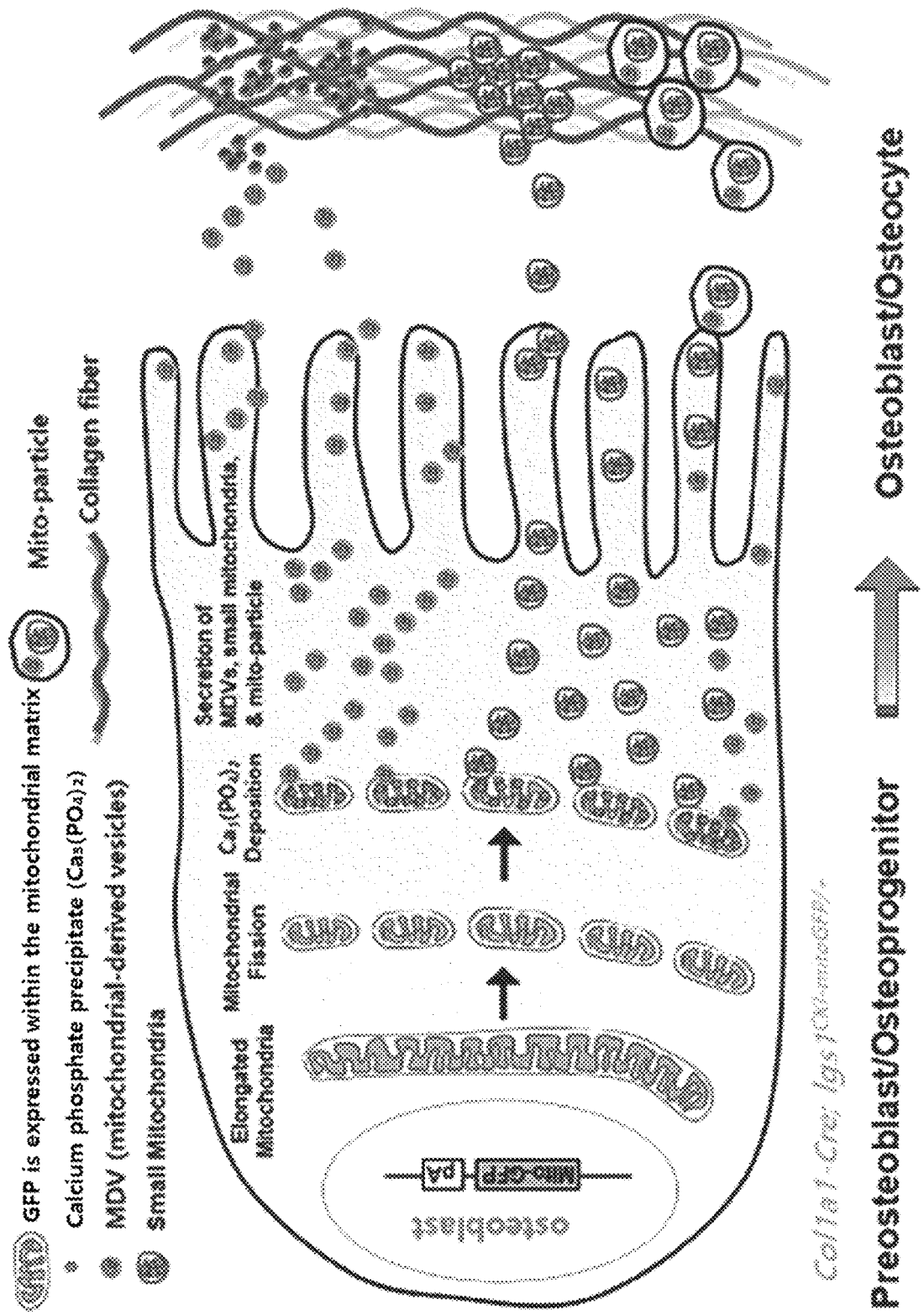

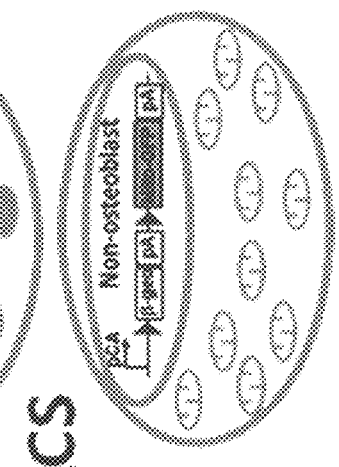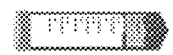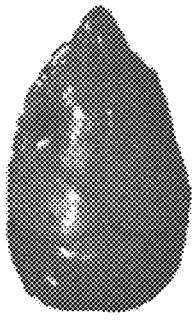
FIG.6a

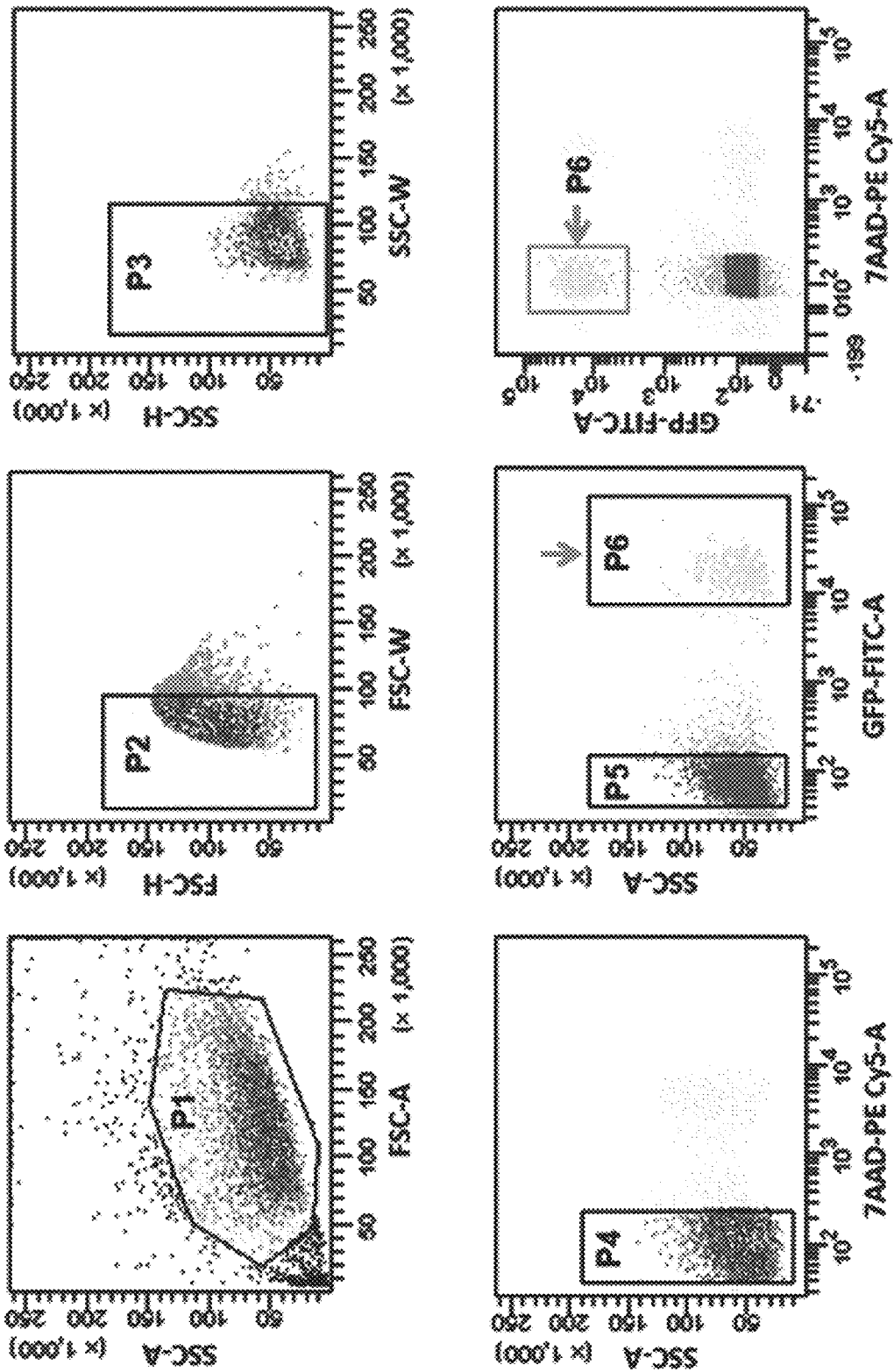

| Population | #Events | %Parent | %Total |
|---|---|---|---|
| All Events | 10,000 | | 100.0 |
| P1 | 9,247 | 92.5 | 92.5 |
| P2 | 8,797 | 95.1 | 88.0 |
| P3 | 8,665 | 98.5 | 86.6 |
| P4 | 4,654 | 53.7 | 46.5 |
| P5 | 3,332 | 71.6 | 33.3 |
| P6 | 308 | 6.6 | 3.1 |

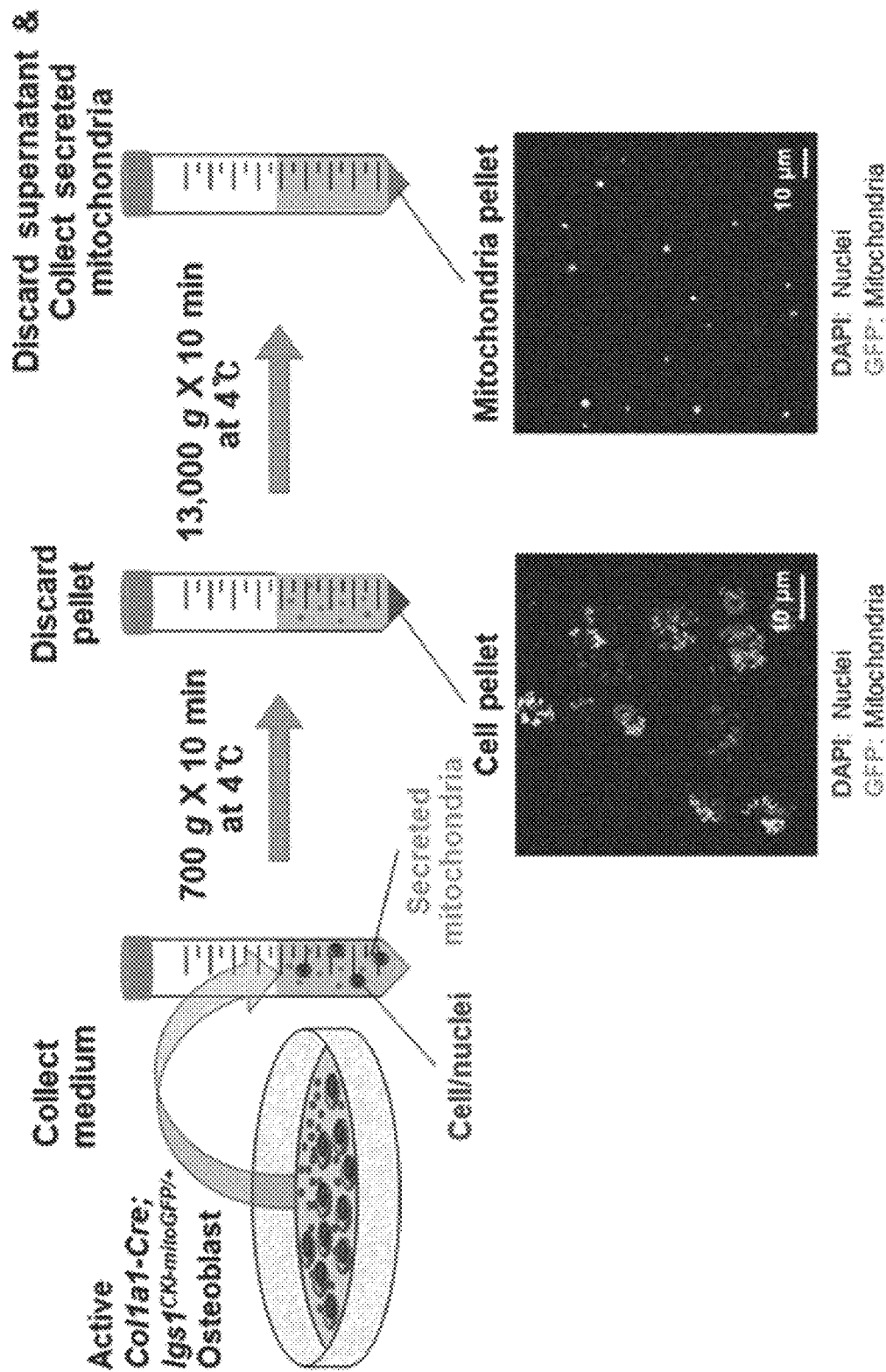

PHARMACEUTICAL COMPOSITION FOR PROMOTING OSTEOGENESIS, COMPRISING OSTEOBLAST-DERIVED MITOCHONDRIA

TECHNICAL FIELD

A pharmaceutical composition for promoting osteogenesis and a pharmaceutical composition for treating bone disease, comprising osteoblast-derived mitochondria as an active ingredient. The osteoblast-derived mitochondria may promote bone regeneration and/or osteogenesis, enhance bone density, and be usefully used for prevention and/or treatment of bone disease.

BACKGROUND ART

Mitochondria are essential organelles for the survival of eukaryotic cells involved in synthesis and regulation of adenosine triphosphate (ATP) as an energy source. Mitochondria are involved in the control of various metabolic pathways in vivo, such as cell signaling, cell differentiation, apoptosis, as well as the cell cycle and cell growth.

Therefore, when mitochondria are damaged, various diseases may be caused, and most known mitochondrial disorders are due to hereditary or acquired mutations occurring in mitochondrial DNA. For example, mitochondrial function may be modified by swelling due to abnormal mitochondrial membrane potential, oxidative stress by reactive oxygen species or free radicals, and defects in oxidative phosphorylation for mitochondrial energy generation, and the like.

Mitochondria also constantly communicate with surrounding organelles, and in this process, they secrete their own vesicles to exchange various substances. Mitochondria are also known to be able to be transferred between cells in the forms of small mitochondria (generated by mitochondrial fission) or vesicles (derived from mitochondria).

According to the study of Hayakawa et al., healthy mitochondria or mitochondria-derived vesicles secreted from healthy astrocytes may be transmitted to neurons damaged by stroke (Nature. 2016 Jul. 28; 535(7613):551-5).

On the other hand, proper maintenance of the shape and function of bones constituting the skeleton of vertebrates is essential for maintaining life, and osteoblasts, cells that form bones, control the secretion of various substances to optimally maintain the state of these bones.

In mineralization of bones, various substances including calcium phosphate, an important component of hydroxyapatite $(Ca_{10}(PO_4)_6(OH)_2)$ in bone tissue, are produced inside osteoblasts and are secreted to the extracellular matrix (ECM), and then contribute to the formation of mature bone tissue, but the exact mechanism of how these substances are transported out of cells is still unknown.

Most of the studies observing differentiation and bone mineralization process of osteoblasts evaluated the status of osteoblasts at a relatively late stage after about 3 weeks from the start of osteogenic induction. Therefore, reports on the initial differentiation process and initial process of calcium phosphate formation in osteoblasts are insufficient so that it has been difficult to detect early bone lesions and develop treatments.

DISCLOSURE

Technical Problem

In the present description, by discovering that osteoblast-derived mitochondria contribute to osteogenesis, it is suggested that it can be usefully applied to the treatment of bone disease by promoting osteogenesis through mitochondria activation and inducing bone mineralization in bone defects.

One example provides a pharmaceutical composition for osteogenesis, comprising osteoblast-derived mitochondria as an active ingredient.

The osteoblast-derived mitochondria,
may comprise
(1) mitochondria isolated or secreted from an osteoblast, an osteoblast culture, or an osteoblast crushed material,
(2) a vesicle derived from the mitochondria of the (1) (mitochondria-derived vesicle, MDV), or
(3) a combination of the (1) and (2).

The pharmaceutical composition may have an effect of osteogenesis or promoting osteogenesis and/or prevention and/or treatment of bone disease. Accordingly, another example provides a pharmaceutical composition for osteogenesis or promoting osteogenesis comprising osteoblast-derived mitochondria as an active ingredient. Other example provides a pharmaceutical composition for osteogenesis or prevention and/or treatment of bone disease comprising osteoblast-derived mitochondria as an active ingredient.

Other example provides a method for osteogenesis and/or prevention and/or treatment of bone disease comprising administering a pharmaceutically effective dose of osteoblast-derived mitochondria to a subject in need of osteogenesis or promoting osteogenesis and/or prevention and/or treatment of bone disease.

Other example provides a use for using in osteogenesis or promoting osteogenesis and/or prevention and/or treatment of bone disease, or preparation of a pharmaceutical composition for osteogenesis or promoting osteogenesis and/or prevention and/or treatment of bone disease of osteoblast-derived mitochondria.

Other example provides a method for preparation of a pharmaceutical composition for osteogenesis and/or prevention and/or treatment of bone disease comprising osteoblast-derived mitochondria, comprising the extraction of mitochondria from an osteoblast culture.

Technical Solution

In the present description, a use for osteogenesis or promoting osteogenesis and/or prevention and/or treatment of bone disease of osteoblast-derived mitochondria is provided.

Hereinafter, the present invention will be described in more detail.

Osteoblast-Derived Mitochondria

In the present description, osteoblast-derived mitochondria used as an active ingredient may be obtained from osteoblasts of a mammal, for examples, human. In one example, the mitochondria may be isolated from osteoblasts or a culture solution of a mammal, for example, human. In addition, the osteoblast-derived mitochondria may be normal mitochondria obtained from osteoblasts with normal biological activity of mitochondria. Furthermore, the mitochondria derived from osteoblast may be obtained from osteoblasts isolated from a living body and/or osteoblasts cultured in vitro after being isolated from a living body.

The osteoblast-derived mitochondria may be isolated from osteoblasts by various known methods, for example, using a specific buffer solution or using centrifugation and magnetic fields, and the like.

In the present description, the osteoblast-derived mitochondria are a generic term for structures which are derived from osteoblasts and the matrix of mitochondria is surrounded by mitochondrial double membrane (inner and outer membranes). The osteoblast-derived mitochondria may be present in the osteoblasts, or be present in a culture solution (or medium) by being secreted from osteoblasts. In the present description, 'derived from osteoblasts' may mean being present in osteoblasts, or being isolated and/or secreted from osteoblasts, an osteoblast culture, an osteoblast lysate and/or an osteoblast crushed material. For example, the osteoblast-derived mitochondria may comprise one or more kinds selected from the group consisting of mitochondria isolated and/or secreted from osteoblasts, an osteoblast culture, an osteoblast lysate and/or an osteoblast crushed material, vesicles derived from the mitochondria, cells containing the mitochondria and/or mitochondria-derived vesicles (for example, osteoblasts with increased mitochondrial biogenesis), or a culture of the cells, or the like.

In the present description, osteoblasts are cells that make osteocytes in vertebrates, and they are cells which generate bones by synthesizing and secreting bone matrix and calcify bone tissue by depositing minerals such as Ca ions and Mg ions necessary for bone, and become normal osteocytes themselves by being buried in bone tissue created by themselves. Osteoblasts are positioned inside the bone membrane covering bones. The osteoblasts used in the present description may be osteoblasts extracted (or isolated) from bones or osteoblasts cultured in a medium for osteogenic differentiation (also referred to as activated osteoblasts in the present description).

In the present description, mitochondria are organelles comprising a double membrane of inner and outer membranes consisting of phospholipid bilayers, matrix inside the inner membrane, and intermembrane space between the inner membrane and outer membrane, and a portion of the inner membrane protrudes inward to form a 'cristae' structure that is folded in several layers, and the average length of the longest part may be about 10 nm to about 50 um, about 10 nm to about 30 um, about 10 nm to about 10 um, about 50 nm to about 50 um, about 50 nm to about 30 um, or about 50 nm to about 10 um. The mitochondria may comprise mitochondria inside osteoblasts, mitochondria secreted from osteoblasts, mitochondria produced by fission of the mitochondria (having a cristae structure of the inner membrane in a form that the mitochondrial matrix is covered with a double membrane and generally, being spherical and having a relatively small size) or all of them.

The mitochondria-derived vesicle (mitochondria-derived vesicle; MDV) is a part of the mitochondrial matrix separated as covered by a double membrane or single membrane (for example, any one of the outer membrane and inner membrane of the double membrane), and the cristae structure of the inner membrane is not observed, and the average length may be smaller than the mitochondria.

Obtaining Osteoblast-Derived Mitochondria

The mitochondria (mitochondria and/or mitochondria-derived vesicles) derived from osteoblasts may be obtained from osteoblasts, an osteoblast lysate and/or an osteoblast crushed material. In one example, the osteoblast culture may be osteoblasts cultured in a common medium, for example, a medium for osteogenesis or medium for osteogenic differentiation commonly used for osteogenesis and/or osteogenic differentiation.

In one specific example, the osteoblast-derived mitochondria used as an active ingredient in the pharmaceutical composition or method provided in the present description may be used in a form of a pellet obtained by secondary centrifugation of supernatant obtained by primary centrifugation of the culture of osteoblasts, osteoblast lysate, osteoblast crushed material or lysate, or suspension comprising the pellet.

In another example, a method for preparation of osteoblast-derived mitochondria comprising the following steps:
  conducting a primary centrifugation of a culture, crushed material, or lysate of an osteoblast;
  conducting a secondary centrifugation of a supernatant obtained by the primary centrifugation; and
  isolating the sedimented pellet finally.

In obtaining osteoblast-derived mitochondria in the present description, the primary centrifugation is a step for removing cell components other than mitochondria (mitochondria and/or mitochondria-derived vesicles) (for example, cell components larger or heavier than the mitochondria) by sedimentation, and the secondary centrifugation is a step for collecting the mitochondria (mitochondria and/or mitochondria-derived vesicles) in the supernatant obtained in the primary centrifugation by sedimentation, and it may be performed at a higher rate and/or for a longer time than the primary centrifugation. To increase the amount and/or purity of the collected mitochondria (mitochondria and/or mitochondria-derived vesicles), the primary centrifugation (low speed centrifugation) and/or secondary centrifugation (high speed centrifugation) may be performed once or more (for example, once, twice, three times, 4 times or 5 times) each independently.

In one example, after the secondary centrifugation, a common purification step for using the collected mitochondria (mitochondria and/or mitochondria-derived vesicles) as a pharmaceutical composition may be further comprised.

Specifically, the primary and secondary centrifugations may be, each independently, performed at a temperature of 0 to 10° C., 3 to 10° C., 0 to 5° C., or 3 to 5° C. In addition, the primary and secondary centrifugations may be, each independently, performed for 1 to 50 minutes, 1 to 30 minutes, 1 to 15 minutes, 5 to 50 minutes, 5 to 30 minutes, or 5 to 15 minutes, but not limited thereto, and it may be appropriately adjusted according to the number of centrifugations and the content of the sample, and the like.

In one example, they may be performed by increasing the speed from the primary centrifugation to the secondary centrifugation. For example, the primary centrifugation may be performed at a speed of 100 to 2,000×g, 100 to 1,500×g, 100 to 1,000×g, 100 to 800×g, 200 to 2,000×g, 200 to 1,500×g, 200 to 1,000×g, 200 to 800×g, 300 to 2,000×g, 300 to 1,500×g, 300 to 1,000×g, 300 to ×g, 400 to 2,000×g, 400 to 1,500×g, 400 to 1,000×g, 400 to 800×g, 500 to 2,000×g, 500 to 1,500×g, 500 to 1,000×g, 500 to 800×g, 600 to 800×g, 200 to 450×g, or 300 to 450×g. In addition, the secondary centrifugation may be performed at a faster speed than the primary centrifugation, and for example, it may be performed at a speed of 3,000 to 20,000×g, 3,000 to 18,000×g, 3,000 to 16,000×g, 3,000 to 14,000×g, 5,000 to 20,000×g, 5,000 to 18,000×g, 5,000 to 16,000×g, 5,000 to 14,000×g, 7,000 to 20,000×g, 7,000 to 18,000×g, 7,000 to 16,000×g, 7,000 to 14,000×g, 10,000 to 20,000×g, 10,000 to 18,000×g, 10,000 to 16,000×g, 10,000 to 14,000×g.

In one example, the osteoblast-derived mitochondria may be obtained in a culture solution collected after culturing osteoblasts or a form comprised in an osteoblast culture solution. The osteoblast culture solution may be a culture obtained by culturing osteoblasts in a common medium, for example, a commonly used medium for osteocyte differentiation. In this culture solution, cytokines, chemokines, exosomes and microvesicles secreted from cells, and osteoblast-derived mitochondria may be comprised. In one specific example, the isolated of the osteoblast-derived mitochondria may be performed by culturing osteoblasts and primary centrifugation of the obtained culture solution to precipitate cell components other than mitochondria and obtain supernatant, and collecting a fraction (pellet) comprising mitochondrial components by secondary centrifugation of the supernatant.

Medical Use

The osteoblast-derived mitochondria may be used for osteogenesis or promoting osteogenesis and/or prevention and/or treatment of bone disease.

In the present description, osteogenesis or promoting osteogenesis are interchangeable in the same sense and collectively refer to all processes in which new bones are made or produced bones are densified, and it may mean an action that induces and/or promotes one or more selected from all mechanisms accompanied by osteogenesis such as differentiation from osteoblasts to osteocytes, bone mineralization, and the like.

In the present description, the bone disease to which the osteoblast-derived mitochondria may be effectively applied may mean all diseases related to reduction of bone generation/bone regeneration and/or destruction of a normal structure of bone tissue due to one or more selected from the group consisting of reduction of the activity of osteoblasts, an increase of the activity of osteoclasts, external shock, aging, and the like. For example, the bone disease may be one or more selected from the group consisting of fracture, osteoclasia (e.g., secondary osteoclasia, inflammatory osteoclasia, etc.), osteoporosis, osteomalacia, osteoarthritis, rheumatoid arthritis, or osteodystrophy (e.g., reduction of bone regeneration ability due to aging, etc.), and the like.

Unless otherwise mentioned in the present description, the term "active ingredient" refers to a component that exhibits activity alone or exhibits activity together with an adjuvant (carrier) that is inactive by itself. In the present description, the aforementioned osteoblast-derived mitochondria are used as an active ingredient.

In the pharmaceutical composition and prevention/treatment method provided in the present description, the active ingredient, osteoblast-derived mitochondria may be contained or used in a pharmaceutically effective dose. The pharmaceutically effective dose means a content or dose of an active ingredient capable of obtaining a desired effect. The content or dose of the active ingredient (osteoblast-derived mitochondria) in the pharmaceutical composition may be variously prescribed by factors such as formulation method, administration method, patient's age, weight, gender, medical condition, food, administration time, administration interval, administration route, excretion rate and response sensitivity. For example, one dose of the active ingredient may be in a range of 0.001 to 1000 mg/kg, 0.01 to 100 mg/kg, 0.01 to 50 mg/kg, 0.01 to 20 mg/kg, 0.01 to 10 mg/kg, 0.01 to 5 m g/kg, 0.1 to 100 mg/kg, 0.1 to 50 mg/kg, 0.1 to 20 mg/kg, 0.1 to 10 mg/kg, 0.1 to 5 mg/kg, 1 to 100 mg/kg, 1 to 50 mg/kg, 1 to 20 mg/kg, 1 to 10 mg/kg, or 1 to 5 mg/kg, but not limited thereto. In other example, the content of the active ingredient in the pharmaceutical composition may be 0.01% by weight to 99.9% by weight, 0.01% by weight to 90% by weight, 0.01% by weight to 80% by weight, 0.01% by weight to 70% by weight, 0.01% by weight to 60% by weight, 0.01% by weight to 50% by weight, 0.01% by weight to 40% by weight, 0.01% by weight to 30% by weight, 1% by weight to 99.9% by weight, 1% by weight to 90% by weight, 1% by weight to 80% by weight, 1% by weight to 70% by weight, 1% by weight to 60% by weight, 1% by weight to 50% by weight, 1% by weight to 40% by weight, 1% by weight to 30% by weight, 5% by weight to 99.9% by weight, 5% by weight to 90% by weight, 5% by weight to 80% by weight, 5% by weight to 70% by weight, 5% by weight to 60% by weight, 5% by weight to 50% by weight, 5% by weight to 40% by weight, 5% by weight to 30% by weight, 10% by weight to 99.9% by weight, 10% by weight to 90% by weight, 10% by weight to 80% by weight, 10% by weight to 70% by weight, 10% by weight to 60% by weight, 10% by weight to 50% by weight, 10% by weight to 40% by weight, or 10% by weight to 30% by weight, based on the total pharmaceutical composition weight, but not limited thereto.

The pharmaceutical composition provided in the present description, may further comprise a pharmaceutically acceptable carrier, in addition to the active ingredient. The carrier is commonly used for formulation of a drug comprising protein, nucleic acid and/or cells, and may be one or more kinds selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water (for example, water for injection, purified water, etc.), syrup, methyl cellulose, methyl hydroxybenzoate, propyl hydroxybenzoate, talc, magnesium stearate, mineral oil and the like, but not limited thereto. In addition, the pharmaceutical composition may comprise a stabilizer or solubilizer, and for example, the stabilizer may be sodium pyrosulfite or ethylenediaminetetraacetic acid, and the solubilizer may be hydrochloric acid, acetic acid, sodium hydroxide, sodium bicarbonate, sodium carbonate, or potassium hydroxide. The pharmaceutical composition may also, further comprise one or more kinds selected from the group consisting of a diluent, an excipient, a lubricant, a wetting agent, a sweetener, a flavoring agent, an emulsifier, a suspending agent, a preservative and the like.

The subject for the administration of the active ingredient or pharmaceutical composition comprising the same provided in the present description may be a mammal including primates comprising humans, monkeys, and the like, rodents comprising mice, rats, and the like, and so one, or a cell, tissue, cell culture or tissue culture derived therefrom. More specifically, the administration subject of the active ingredient or pharmaceutical composition may be a mammal such as human in need of osteogenesis or having a risk of suffering from bone disease, or suffering from bone disease.

The active ingredient or pharmaceutical composition provided in the present description may be administered by parenteral administration, or be administered by contacting with a cell, tissue or body fluid in a living body or isolated from a living body. Specifically, the active ingredient or pharmaceutical composition may be parenterally administered, for example, directly administered (for example, injected) to a site requiring osteogenesis and/or a bone disease site. In this case, the active ingredient or pharmaceutical composition may be formulated in a form of an injection which can be directly administered (for example, injected) to a diseased area, that is, a site requiring osteogenesis and/or a bone disease site. In this case, the injection may be prepared as a physically or chemically very stable injection, by adjusting pH using a buffer solution such as an acidic aqueous solution or phosphate, and the like, which can be used for injection, to ensure product stability according to the prescription and distribution of the injection.

Specifically, the injection may comprise water for injection. The water for injection is distilled water created to dissolve a solid injection or dilute an aqueous injection, and may be a glucose injection, a xylitol injection, a D-mannitol injection, a fructose injection, physiological saline solution, a dextran 40 injection, a dextran 70 injection, an amino acid injection, Ringer solution, lactic acid-Ringer solution or a phosphate buffer solution in a range of pH 3.5~7.5 or a sodium dihydrogen phosphate-citrate buffer solution, and the like.

In other example, the active ingredient or pharmaceutical composition provided in the present description may be directly administered (attached, inserted or transplanted) in various forms (for example, hydrogel, patch, sheet for transplant, etc.) into a diseased area, that is, a site (tissue) requiring osteogenesis and/or a bone disease site (tissue). In one example, the active ingredient or pharmaceutical composition may be applied (attached, inserted or transplanted) to a diseased area by being comprised in a collagen sheet.

Isolation of Osteoblasts

In the present description, a method for isolating osteoblasts is provided.

The method for isolating osteoblasts comprises the following steps:
  (a) crossing a transgenic animal (the first transgenic animal) engineered to conditionally express a fluorescent protein within the mitochondrial matrix of the cells expressing Cre recombinase and a transgenic animal (the second transgenic animal) engineered to osteoblast-specifically express Cre recombinase, to prepare a transgenic animal (the third transgenic animal) expressing the fluorescent protein only in osteoblasts or mitochondrial matrix of osteoblasts; and
  (b) isolating osteoblasts expressing the fluorescent protein from bone samples (for example, skull fragment, etc.) obtained from the prepared transgenic animal (the third transgenic animal).

The first transgenic animal and the second transgenic animal are animals of the same species that can be crossed, and may be selected from mammals other than humans, for example, mice, rats, rabbits, pigs, dogs or cattle, but not limited thereto. In one example, they may be crossed using a female as the first transgenic animal (expressing a fluorescent protein conditionally with Cre recombinase expression) and using a male as the second transgenic animal (expressing Cre recombinase only in osteoblasts).

The step (b) of isolating osteoblasts expressing then fluorescent protein may comprise extracting cells exhibiting a fluorescent signal from a lysate obtained by treating protease (for example, trypsin, collagenase, etc.) to a bone sample isolated from the third transgenic animal, and the extracting cells exhibiting a fluorescent signal may be performed by a common cell isolation technique such as FACS (Fluorescence-activated cell sorting), and the like.

By the method for isolating osteoblasts as above, live osteoblasts can be isolated.

Since the method for isolating osteoblasts provided in the present description does not require an antibody binding to osteoblasts, it is possible to overcome the problem caused by the absence of an antigen specifically expressed on the outer cell membrane of living osteoblasts during isolation of osteoblasts by FACS using a conventional antibody and/or an antibody binding thereto.

Advantageous Effects

The pharmaceutical composition comprising osteoblast-derived mitochondria (mitochondria and/or mitochondria-derived vesicle) as an active ingredient described in the present invention may induce osteogenic differentiation/osteogenesis in osteoblasts to enhance the osteogenic potential, thereby obtaining an excellent therapeutic effect in various bone diseases.

BRIEF DESCRIPTION OF THE DRAWINGS

FIG. 2 is an ultra high resolution fluorescence microscope Lattice SIM (structured illumination microscopy) image observing fission of mitochondria after induction of osteogenesis of osteoblasts extracted from skull of the transformed mouse (Col1a1-Cre; Igs1$^{CKI\text{-}mito\text{-}GFP/+}$).

FIG. 4a is images observing inside of the osteoblasts at 25,000 magnifications (left) and 15,000 magnifications (right), respectively (bar scale: 500 nm), and FIG. 4b is an image observing inside of the osteoblasts at 10,000 magnifications (bar scale: 1 μm), and FIG. 4c are images observing outside of the osteoblasts at 10,000 magnifications (left) and 6000 magnifications (right), respectively (left photograph: top arrow—collagen fiber, bottom arrow—Extracellular mitochondria, bar scale—1 μm; right photograph (osteoid): top arrow—mineral deposition, middle—collagen fiber, bottom arrow—Extracellular mitochondria, bar scale—2 μm).

FIG. 5 is a mimetic diagram summarizing and showing a hypothesis that mitochondria-derived vesicles (MDVs) and small mitochondria secreted from osteoblasts extracted from the skull of the transformed mouse (Col1a1-Cre; Igs1$^{CKI\text{-}mito\text{-}GFP/+}$) induce osteogenesis.

FIG. 6a mimetically shows the process of extracting osteoblasts using fluorescence-activated cell sorting (FACS) from cells extracted from the skull of the transformed mouse (Col1a1-Cre; Igs1$^{CKI\text{-}mito\text{-}GFP/+}$).

FIG. 6b and FIG. 6c show the result of quantifying the FACS result of FIG. 6a.

FIG. 6d is a fluorescent image obtained by the FACS result of FIG. 6a-c and shows osteoblasts in which green fluorescent protein (GFP) is expressed within the mitochondrial matrix (bar scale: 50 μm).

FIG. 7 is a mimetic diagram showing the process of isolating mitochondria and mitochondria-derived vesicles (MDVs) secreted from the activated osteoblasts.

MODE FOR INVENTION

Hereinafter, preferable examples are presented to help understanding of the present invention. However, the following examples are only provided for easier understanding of the present invention, and the contents of the present invention are not limited by the following examples.

Figure 1:
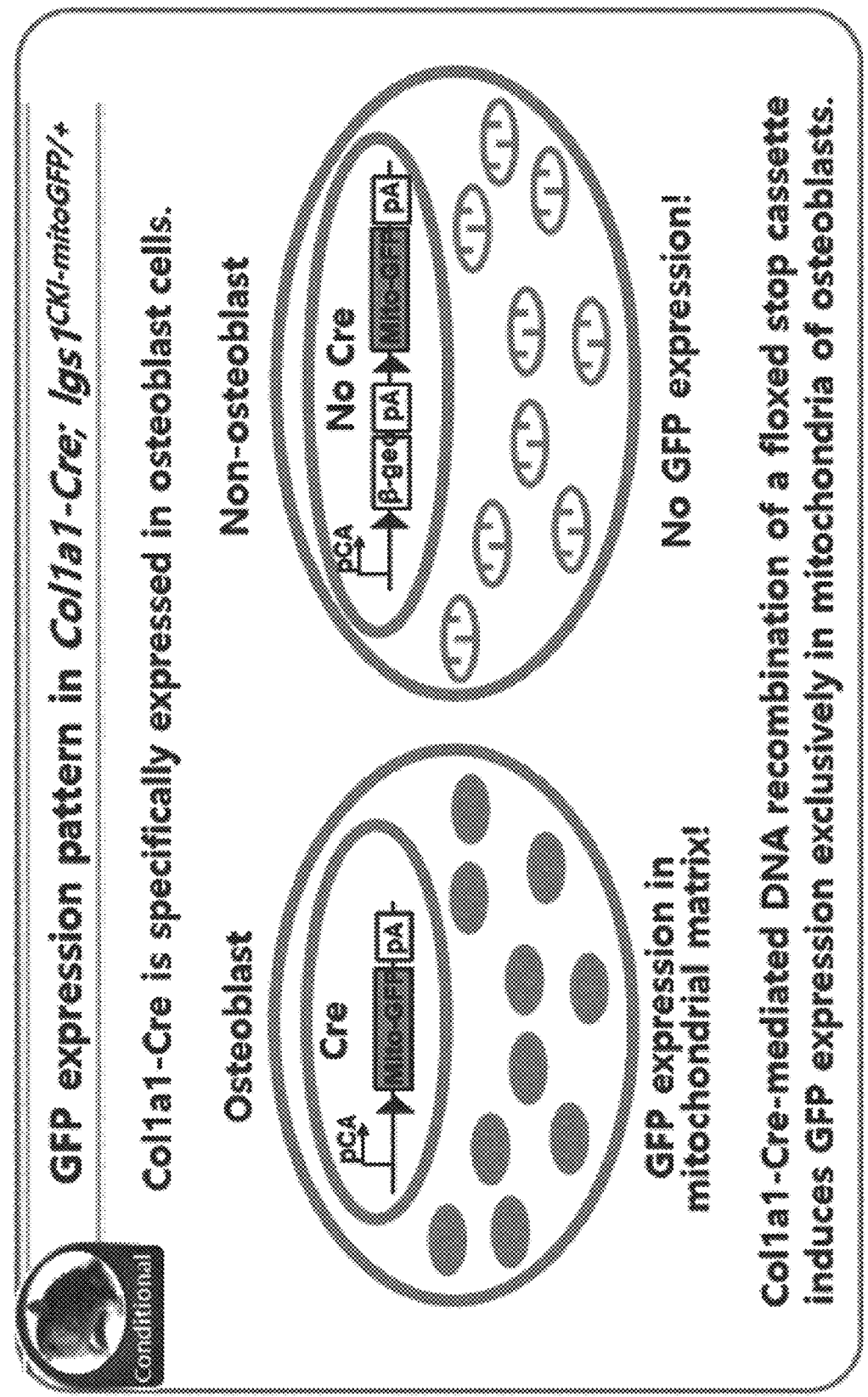
FIG. 1 is a mimetic diagram illustratively showing the production process of a conditionally engineered mouse (Col1a1-Cre; Igs1$^{CKI\text{-}mito\text{-}GFP/+}$) in which green fluorescent protein (GFP) is selectively expressed only in the mitochondria of osteoblasts for selective isolation of osteoblasts.

Example 1: Confirmation of Mitochondrial Fission After Induction of Osteoblast Differentiation in Skull-Derived Osteoblasts For secretion and confirmation of osteoblast-derived mitochondria and mitochondria-derived vesicles, a transformed mouse in which green fluorescent protein (GFP) was expressed specifically in the mitochondrial matrix of the osteoblasts was produced. More specifically, a transformed mouse (Col1a1-Cre; $Igs1^{CKI\text{-}mito\text{-}GFP/+}$) conditionally expressing GFP only in the mitochondria of the osteoblasts was produced by crossing a transformed mouse ($Igs1^{CKI\text{-}mitoGFP/CKI\text{-}mitoGFP}$) that expresses GFP only in the mitochondrial matrix of Cre recombinase expressing cells (purchased from Jackson Lab; Stock No. 018140) with Col1a1-Cre mouse that expresses Cre recombinase specifically in osteoblasts (the mouse deposited (freeze-preserved) at Korea Research Institute of Bioscience and Biotechnology was revived with the consent of the depositor) (crossing between female $Igs1^{CKI\text{-}mitoGFP/CKI\text{-}mitoGFP}$ mouse and male Col1a1-Cre mouse). The description of the transformed mice as above is schematically shown in FIG. 1.

First, the impurities were removed from the bone tissue by treating the skull of the transformed mice prepared as above with 0.25% trypsin-EDTA (Gibco) solution for 10 minutes followed by discarding the solution, and then with 2 mg/mL type 2 collagenase (Worthington) solution for 30 minutes followed by discarding the solution, once the impurities were removed, cells can be isolated from the bone tissue with type 2 collagenase treatment for 60 minutes, and collected by centrifugation at a rate of 1300 rpm for 3 minutes. To exclude non-viable cells, all cells extracted from the bone tissue were stained with 7-AAD (7-amino-actinomycin D; Bio-Legend) for about 10 minutes (staining only dead cells), and only viable osteoblasts expressing GFP were isolated using fluorescence-activated cell sorting (FACS). For further details on FACS procedures, cells having similar shape and size were isolated first, and only live cells among these cells (7-AAD negative cells) were selected and separated into cells expressing GFP (osteoblasts) and cells not expressing GFP (non-osteoblasts), and then only the osteoblasts expressing GFP were collected. The skull-derived osteoblasts isolated and extracted like this were cultured in a medium for osteoblast differentiation to induce osteogenic differentiation. The medium for osteoblast differentiation consisted of alpha MEM (Minimum Essential Medium—Alpha Modification; HyClone) in which 50 µg/mL ascorbic acid (Amreasco), 5 mM beta-glycerophosphate (Sigma), 10% (w/v) fetal bovine serum (Gibco), and 100 U/mL°] penicillin-streptomycin (Gibco) were added, and the result of observing differentiated osteoblasts expressing GFP within the mitochondrial matrix with a ultra high resolution fluorescent microscope Lattice SIM (structured illumination microscopy) at 0.5 days and 7 days after osteoblast differentiation was shown in FIG. 2. As shown in FIG. 2, extensive fission of mitochondria in osteoblasts can be confirmed as the differentiation time elapses.

Example 2: Confirmation of Secretion of Vesicles in Mitochondria After Inducing Osteogenic Differentiation in Skull-Derived Osteoblasts As described in Example 1, after inducing osteogenesis for 7 days by culturing the skull-derived osteoblasts extracted from the skull of the transformed mice (Col1a1-Cre; $Igs1^{CKI\text{-}mito\text{-}GFP/+}$) in a medium for osteoblast differentiation, real-time cell photography was performed with an ultra high resolution Lattice SIM (structured illumination microscopy) fluorescent microscope (Elyra 7, Zeiss) for about 20 minutes.

Figure 3:
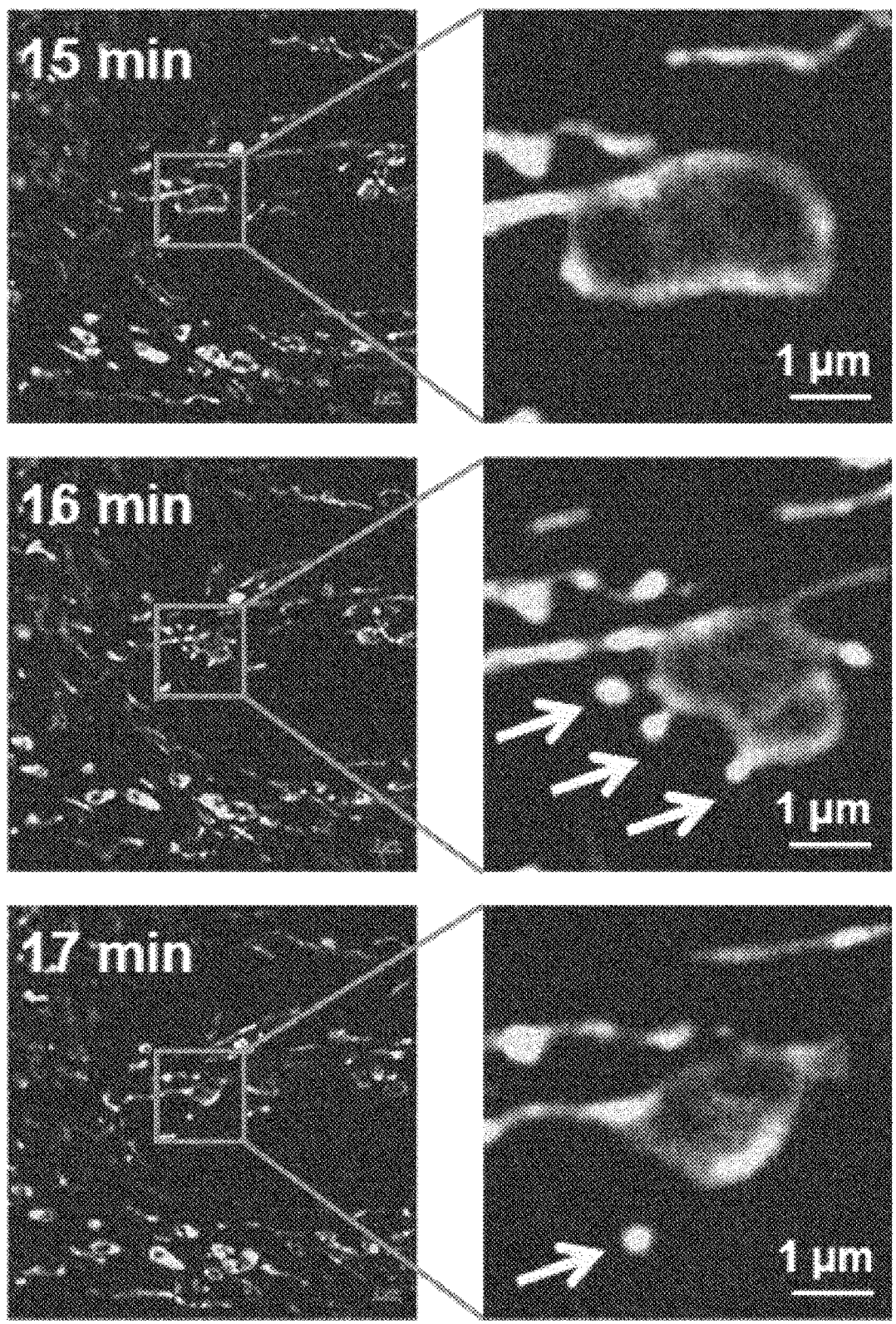
FIG. 3 is an ultra high resolution fluorescence microscope Lattice SIM (Elyra 7, Zeiss) image observing secretion of mitochondria-derived vesicles after inducing osteogenesis in osteoblasts extracted from the skull of the transformed mouse (Col1a1-Cre; Igs1$^{CKI\text{-}mito\text{-}GFP/+}$).

As a result, the obtained fluorescent image was shown in FIG. 3. As shown in FIG. 3, it can be confirmed that small mitochondria or mitochondria-derived vesicle (MDVs) (arrow of FIG. 3) are actively secreted from the mitochondria expressing green fluorescent protein (GFP) within the mitochondrial matrix.

Figure 4A:
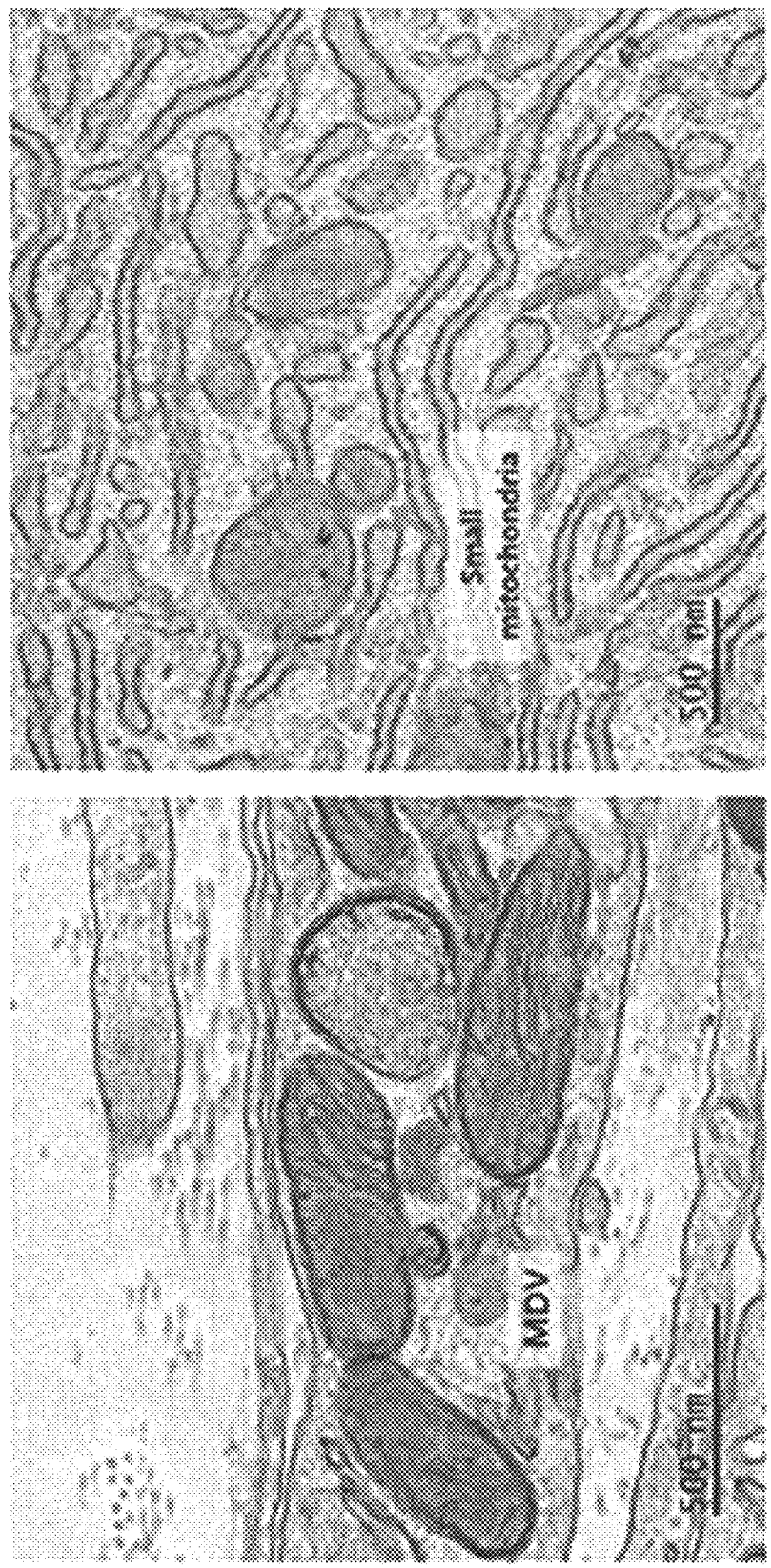
FIG. 4a to FIG. 4c are transmission electron microscope images observing the cell structures inside of the osteoblasts after induction of osteogenesis in osteoblasts extracted from the skull of the transformed mouse (Col1a1-Cre; Igs1$^{CKI\text{-}mito\text{-}GFP/+}$)
Figure 4B:
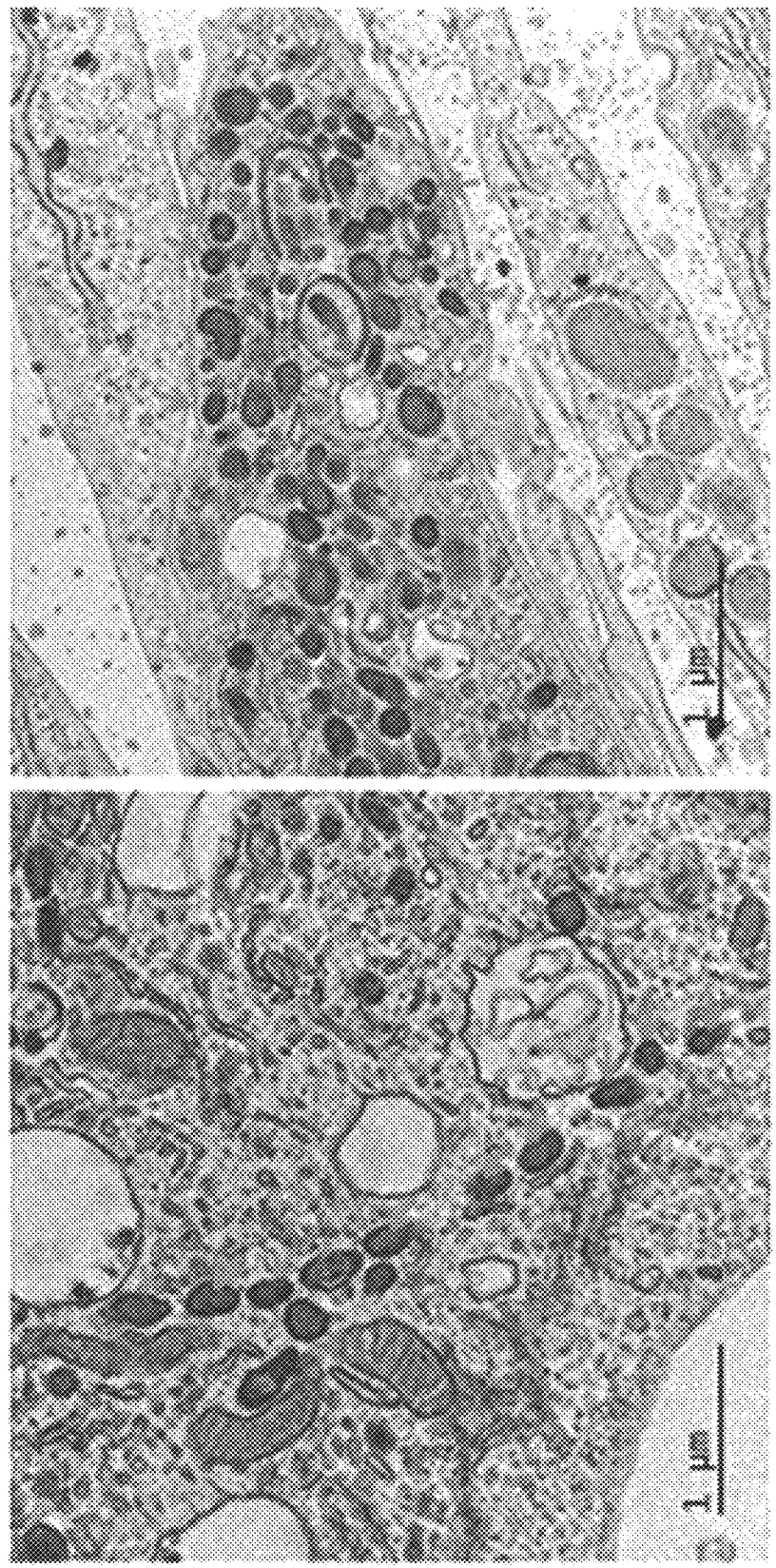
Figure 4C:
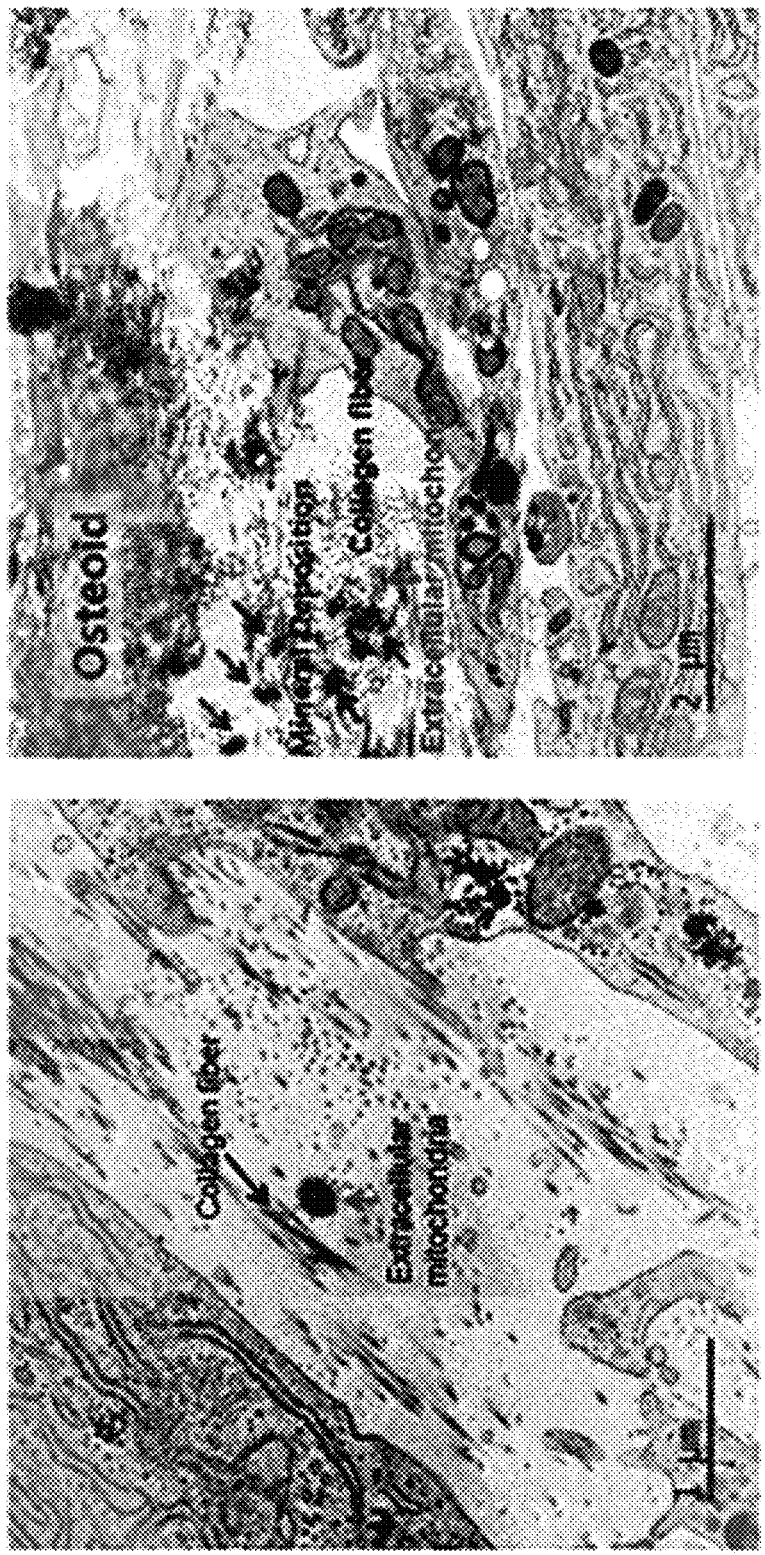

Example 3: Confirmation of Mitochondria-Derived Vesicles Inside and Outside Osteoblasts During Osteoblast Differentiation Process As described in Example 1, after inducing osteogenesis in the osteoblasts extracted from the skull of the transformed mice (Col1a1-Cre; $Igs1^{CKI\text{-}mito\text{-}GFP/+}$), cell structures inside and outside the osteoblasts were observed with a transmission electron microscope, and the result was shown in FIGS. 4a, 4b and 4c. As shown in FIG. 4a, it can be confirmed that mitochondria-derived vesicles and small mitochondria are separated from relatively big mitochondria inside the osteoblasts. As shown in FIG. 4b, it can be confirmed that many small mitochondria that appear dark due to the high electron density are produced inside the osteoblasts. As shown in FIG. 4c, it can be confirmed that mitochondria-derived vesicles and/or small mitochondria are secreted near the collagen fibers outside the osteoblasts at the site where osteogenesis is induced.

Example 4: Confirmation of Pro-Osteogenic Action of Mitochondria Components Secreted in Activated Osteoblasts As shown in the mimetic diagram of FIG. 5, an experiment to demonstrate that mitochondria and mitochondria-derived vesicles secreted from activated osteoblasts induce osteogenesis was conducted. FIG. 5 is a mimetic diagram summarizing the process that mitochondria are extensively divided during the differentiation of activated osteoblasts for osteogenesis, and calcium phosphate is accumulated inside the mitochondria, and then mitochondria-derived vesicles and/or small mitochondria including accumulated calcium phosphate are secreted from osteoblasts to promote bone mineralization together with collagen fibers in the extracellular bone matrix. This suggests that mitochondria, mitochondria-derived vesicles (MDVs) and small mitochondria secreted from the activated osteoblasts may be applied for osteogenic induction.

Figures 6C, 6D:
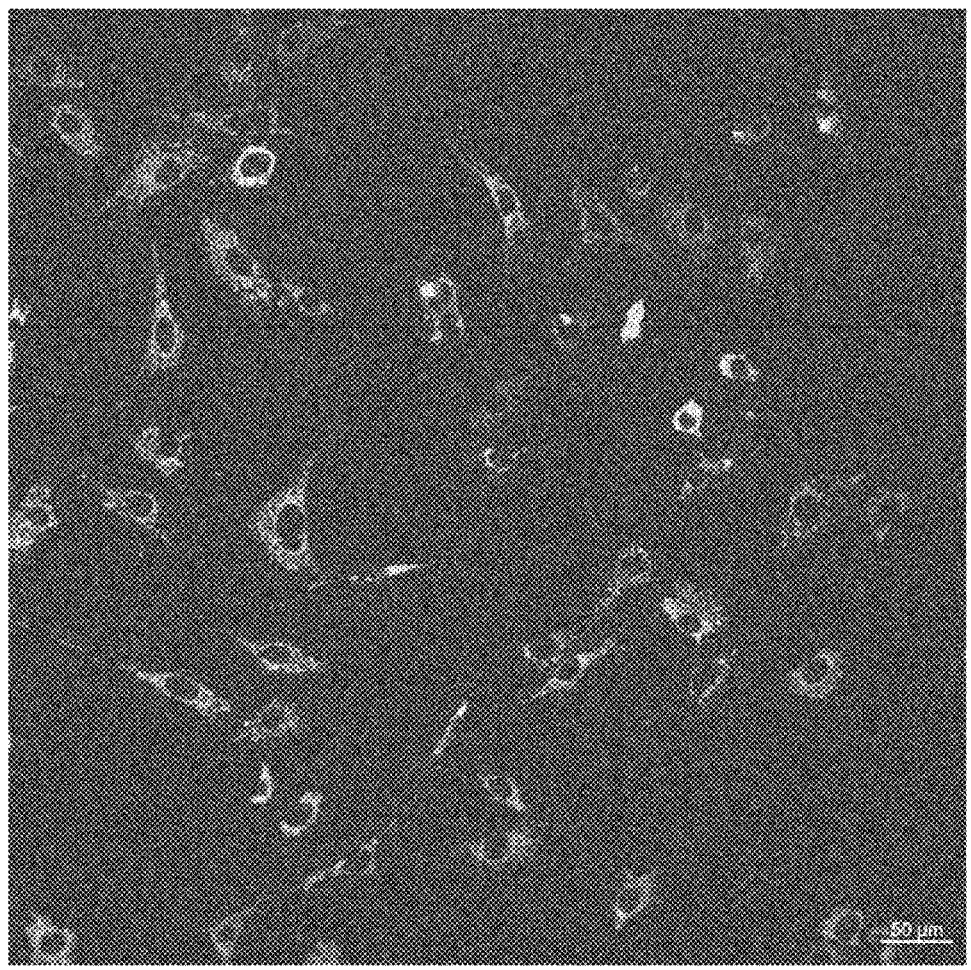

First, osteoblasts were extracted from cells obtained in the skull of the transformed mice (Col1a1-Cre; $Igs1^{CKI\text{-}mito\text{-}GFP/+}$) as shown in Example 1 using fluorescence-activated cell sorting (FACS) (See FIG. 6a). Specifically, cells (P1~P4 of FIG. 6c) having similar size and shape were isolated first, and only live cells obtained from the skull were separated, and among them, only the osteoblasts (GFP positive Osteoblasts; P6 labeled with arrows in FIGS. 6b and 6c) expressing green fluorescent protein were separated. The FACS process and the result of flow cytometry obtained therefrom were shown in FIGS. 6b, 6c and 6d. As shown in FIGS. 6b, 6c and 6d, the separated osteoblasts corresponding to P6 population labeled with arrows account for about 3.1% of the total cells.

In addition, after extracting mitochondria and mitochondria-derived vesicles secreted from the osteoblasts by collecting the culture medium of the activated osteoblasts (osteoblast in which differentiation was induced in a medium for osteoblast differentiation), osteogenesis was evaluated by adding the extracted mitochondria and mitochondria-derived vesicles in the medium for differentiation of osteoblasts. More specifically, after collecting the culture medium of the activated osteoblasts in which differentiation was induced in the medium for osteoblast differentiation, cells were precipitated by refrigerated centrifugation at a rate of 700×g at 4° C. for 10 minutes (indicated as a cell pellet in FIG. 7 (including nuclei)), and by collecting the supernatant, dead cells were discarded, and the collected supernatant was refrigerated centrifuged again at a rate of 13,000×g for 10 minutes, and a pellet (indicated as a mitochondria pellet in FIG. 7; the mitochondrial matrix region was labeled as green (GFP)) comprising mitochondria and mitochondria-derived vesicles was obtained.

After resuspending the obtained pellet (extraction from the differentiation culture solution of 10 mL of a culture dish with a 57.5 cm² area) with a 200 µℓ medium for osteoblast differentiation, they were added to osteoblasts newly inducing osteogenesis in a culture dish with a 0.75 cm² area. For in vivo application in bone defect models, bone defects were filled with collagen sponges soaked in resuspension solution of the obtained pellet to induce osteogenesis. The process of isolating the mitochondria and mitochondria-derived vesicles from the osteoblasts and the obtained result were shown in FIG. 7.

Figure 8A:
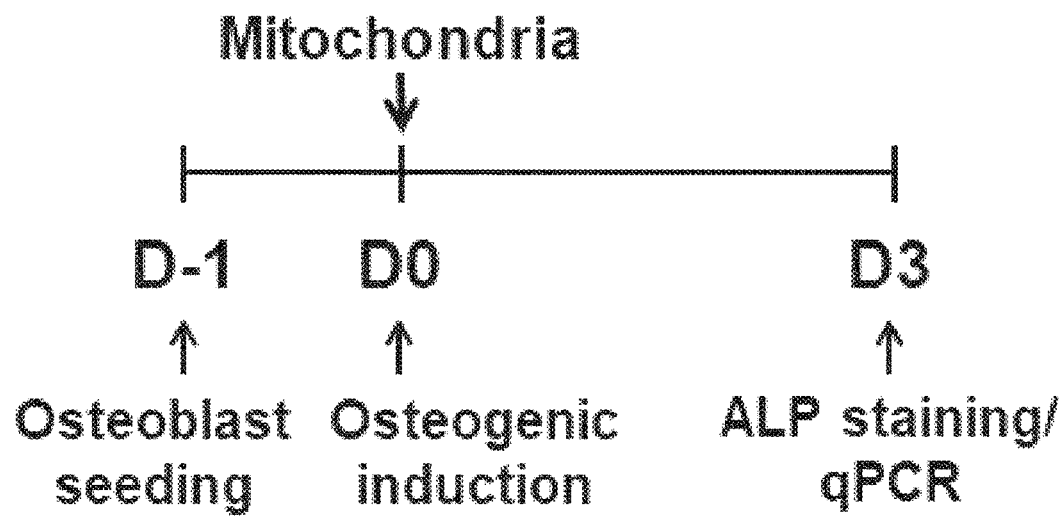
FIG. 8a is a mimetic diagram showing the process of applying the secreted mitochondria and mitochondria-derived vesicles (MDVs) for osteogenic induction.
Figure 8B:
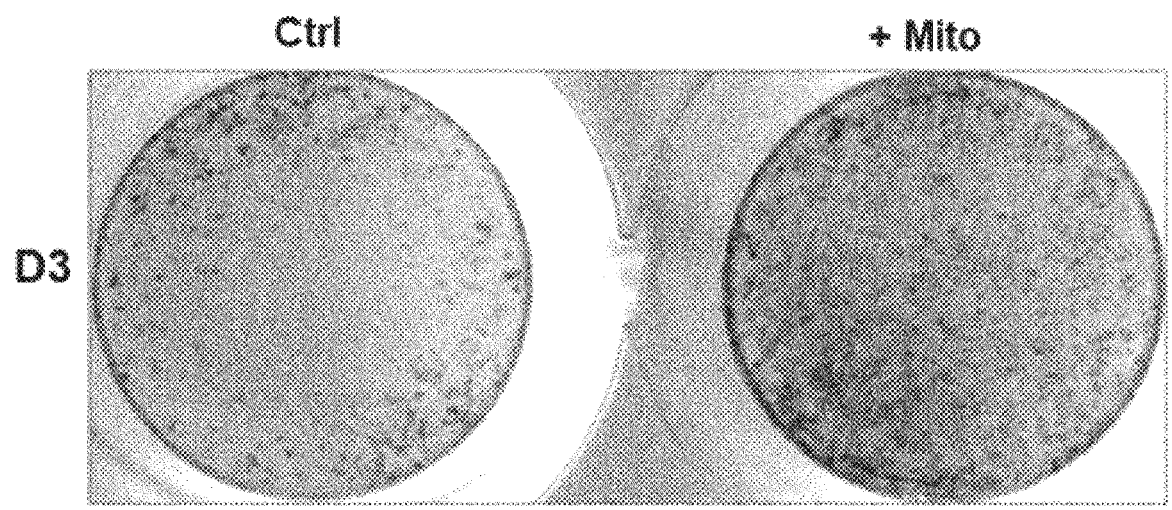
FIG. 8b shows the result of alkaline phosphatase (ALP) staining in 3 days after adding the extracted mitochondria to the osteoblast differentiation culture solution. The osteogenic ability of the osteoblasts grown in the mitochondria-added differentiation culture solution was definitely promoted, compared with the control group.

To confirm the osteogenesis activity of the mitochondria and mitochondria-derived vesicles, an osteogenesis marker, alkaline phosphatase (ALP) was detected. Specifically, as in FIG. 8a, alkaline phosphatase (ALP) staining was performed on the 3$^{rd}$ day after treating a mitochondrial pellet to the culture solution for osteoblast differentiation. The ALP staining was conducted at 37° C. for 30 minutes after dissolving 1 mg Naphthol AS-MX phosphate (Sigma) in 100 µL N,N-dimethylformamide (Sigma) and then adding 2 mL 0.1% Fast blue BB salt (Sigma) solution. For comparison, the same experiment was performed using a culture solution for osteoblast differentiation untreated with a mitochondrial pellet. The obtained result was shown in FIG. 8b. As shown in FIG. 8b, it can be confirmed that the osteogenic ability of osteoblasts grown in the mitochondrial pellet-added culture solution for differentiation was significantly enhanced compared with the control group.

In addition, the osteogenic activity of the mitochondria and mitochondria-derived vesicles isolated from the osteoblasts was measured at an expression level of Alp1, Runx2, and Sp7, which are representative gene markers related to osteoblast differentiation. Specifically, as in FIG. 8a, on the 3$^{rd}$ day after treating the mitochondrial pellet, real-time polymerase chain reaction (qRT-PCR) was performed to measure the expression level of Alp1, Runx2, and Sp7. For comparison, the same experiment was performed using a culture solution for osteoblast differentiation untreated with a mitochondrial pellet. The primer sequences used in the qRT-PCR are as follows: Alp1 F_primer: CCAACTCTTTTGTGCCAGAGA, Alp1 R_primer: GGCTACATTGGTGTTGAGCTTTT, Runx2 F_primer: TTCTCCAACCCACGAATGCAC, Runx2 R_primer: CAGGTACGTGTGGTAGTGAGT, Sp7 F_primer: CGCATCTGAAAGCCCACTTG, Sp7 R_primer: CAGCTCGTCAGAGCGAGTGAA.

Figure 8C:
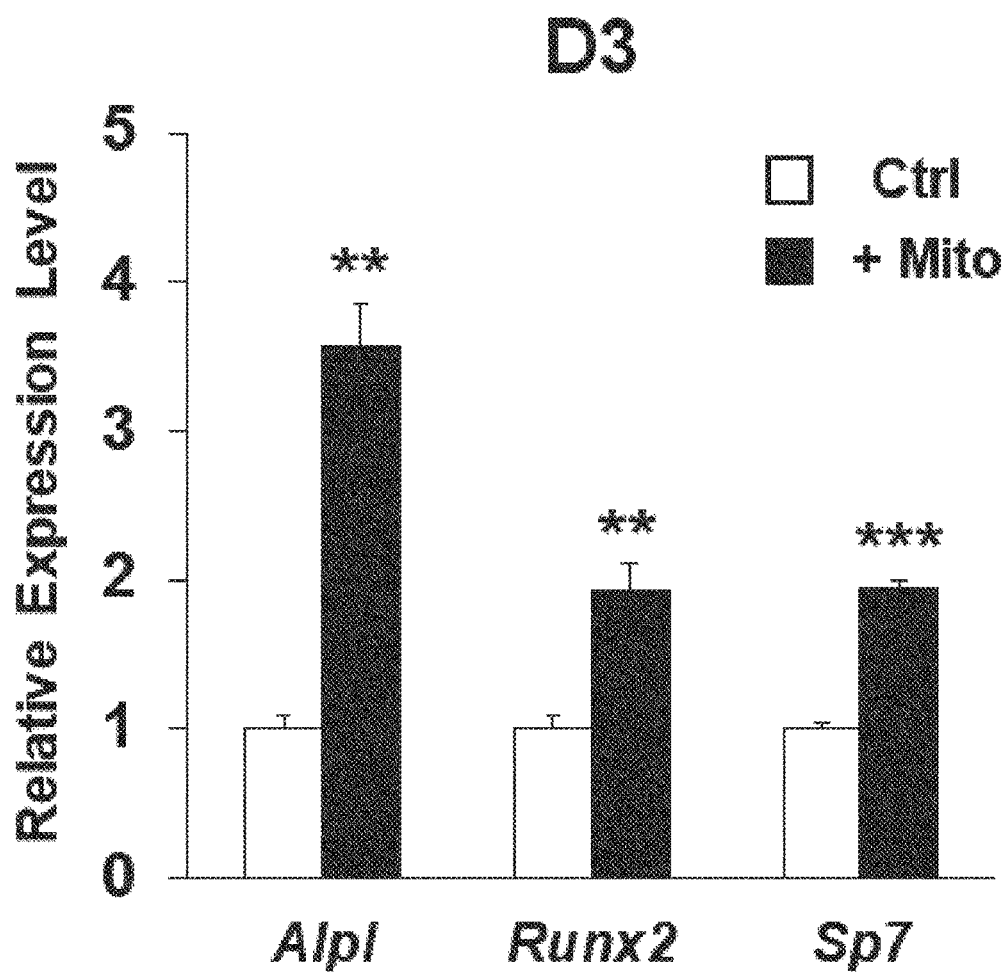
FIG. 8c is a graph showing the result of confirming expression of representative genes (Alp1, Runx2, Sp7) related to the osteoblast differentiation through real-time polymerase chain reaction (qRT-PCR) in 3 days after adding the extracted mitochondria to the osteoblast differentiation culture solution.

The obtained result was shown in FIG. 8c. As shown in FIG. 8c, compared with the control group, it can be confirmed that the expression of the representative genes (Alp1, Runx2, Sp7) related to osteoblast differentiation was significantly increased in the osteoblasts grown in the mitochondrial pellet-added culture solution for differentiation.

The result shown in FIGS. 8b and 8c was obtained in only 3 days after treatment of the mitochondrial pellet extracted from the culture solution for osteoblast differentiation, demonstrating that the mitochondria and mitochondria-derived vesicles extracted from osteoblasts have excellent ability to promote bone formation. This suggests that the mitochondria and mitochondria-derived vesicles extracted from osteoblasts may be a valuable therapeutic option for prevention or treatment of bone disease.

The invention claimed is:

1. A method for promoting osteogenesis, comprising osteoblast-derived mitochondria administration to a subject in need of osteogenesis,
   wherein the osteoblast-derived mitochondria comprise,
   (1) mitochondria isolated or secreted from an osteoblast,
   (2) a vesicle derived from the mitochondria of the (1), or
   (3) a combination of the (1) and (2).

2. The method according to claim 1, wherein the osteoblast-derived mitochondria are in a form of a pellet sedimented by secondary centrifugation of supernatant obtained by primary centrifugation of a culture, lysate or crushed material of an osteoblast or suspension comprising the pellet.

3. The method according to claim 2, wherein the primary centrifugation is performed at a rate of 100 to 2,000×g at 0 to 10° C. for 1 to 50 minutes.

4. The method according to claim 2, wherein the secondary centrifugation is performed at a rate of 3,000 to 20,000×g at 0 to 10° C. for 1 to 50 minutes.

5. A method for treatment of bone disease, comprising osteoblast-derived mitochondria administration to a subject in need of treatment of bone disease,
   wherein the osteoblast-derived mitochondria comprise,
   (1) mitochondria isolated or secreted from an osteoblast,
   (2) a vesicle derived from the mitochondria of the (1), or
   (3) a combination of the (1) and (2).

6. The method according to claim 5, wherein the osteoblast-derived mitochondria are in a form of a pellet sedimented by secondary centrifugation of supernatant obtained by primary centrifugation of a culture, lysate or crushed material of an osteoblast or suspension comprising the pellet.

7. The method according to claim 6, wherein the primary centrifugation is performed at a rate of 100 to 2,000×g at 0 to 10° C. for 1 to 50 minutes.

8. The method according to claim 6, wherein the secondary centrifugation is performed at a rate of 3,000 to 20,000×g at 0 to 10° C. for 1 to 50 minutes.

9. The method according to claim 5, wherein the bone disease is fracture, osteoclasia, osteoporosis, osteomalacia, osteoarthritis, rheumatoid arthritis, or osteodystrophy.

10. A method for preparation of osteoblast-derived mitochondria, comprising primary centrifugation of a culture, lysate or crushed material of an osteoblast;

secondary centrifugation of supernatant obtained by the primary centrifugation; and isolating the sedimented pellet finally, wherein the osteoblast-derived mitochondria comprise, (1) mitochondria isolated or secreted from an osteoblast, (2) a vesicle derived from the mitochondria of the (1), or (3) a combination of the (1) and (2).

11. The method according to claim 10, wherein the primary centrifugation is performed at a rate of 100 to 2,000×g at 0 to 10° C. for 1 to 50 minutes.

12. The method according to claim 10, wherein the secondary centrifugation is performed at a rate of 3,000 to 20,000×g at 0 to 10° C. for 1 to 50 minutes.

13. The method according to claim 10, wherein the osteoblast-derived mitochondria are for use in promoting osteogenesis or treatment of bone disease.

14. A method for isolating osteoblasts, comprising (a) crossing a transgenic animal engineered to conditionally express a fluorescent protein within the mitochondrial matrix of the cells expressing Cre recombinase and a transgenic animal engineered to osteoblast-specifically express Cre recombinase, to prepare a transgenic animal expressing the fluorescent protein only in osteoblasts or mitochondrial matrix of osteoblasts; and (b) isolating osteoblasts expressing the fluorescent protein from bone samples obtained from the prepared transgenic animal.

* * * * *